United States Patent [19]

Bergman

[11] Patent Number: 4,567,894
[45] Date of Patent: Feb. 4, 1986

[54] HYDRAULICALLY OPERATED, MOBILE PATIENT TRANSPORT TABLE USEFUL WITH A MAGNETIC RESONANCE SCANNER

[75] Inventor: Charles T. Bergman, Watertown, Wis.

[73] Assignee: General Electric Company, Milwaukee, Wis.

[21] Appl. No.: 670,460

[22] Filed: Nov. 9, 1984

[51] Int. Cl.⁴ ............................................. A61B 5/05
[52] U.S. Cl. .................... 128/653; 403/325; 403/327; 250/561; 269/322; 60/418
[58] Field of Search ........................ 128/653; 324/309; 403/333, 334, 322, 325, 327, 330; 250/561; 378/208, 209; 269/322; 60/413, 418, 484

[56] References Cited

U.S. PATENT DOCUMENTS

| | | | |
|---|---|---|---|
| 3,495,089 | 2/1970 | Brown | 250/561 |
| 3,508,773 | 4/1970 | Coberly et al. | 403/334 |
| 3,866,899 | 2/1975 | Lee | 269/322 |
| 3,911,679 | 10/1975 | Matthews | 60/418 |
| 4,017,737 | 4/1977 | Hudson et al. | 378/208 |
| 4,131,802 | 12/1978 | Braden et al. | 269/322 |
| 4,225,125 | 9/1980 | Lee | 269/322 |
| 4,320,622 | 3/1982 | Farr | 60/418 |
| 4,346,763 | 8/1982 | Swanson et al. | 60/484 |
| 4,346,778 | 8/1982 | Bluggel et al. | 250/561 |
| 4,362,418 | 12/1982 | Loomis | 403/334 |
| 4,373,816 | 2/1983 | Laib | 250/561 |
| 4,411,270 | 10/1983 | Damadian | 128/653 |
| 4,469,163 | 9/1984 | Klaucic | 403/330 |
| 4,502,807 | 3/1985 | Salice | 403/330 |
| 4,528,510 | 7/1985 | Loeffler et al. | 324/309 |

Primary Examiner—Kyle L. Howell
Assistant Examiner—Ruth S. Smith
Attorney, Agent, or Firm—Alexander M. Gerasimow; Douglas E. Stoner

[57] ABSTRACT

A hydraulically operated, mobile patient transport table useful with a magnetic resonance scanner, which includes a magnet for producing a polarizing magnetic field, employs a hydraulic motor disposed at the base of the magnet and a hydraulic pump disposed at the base of the table. The hydraulic motor and pump are operatively coupled to enable transfer of energy from the motor to the pump without use of hydraulic connections therebetween. In the preferred embodiment, the coupling is implemented with a cone-shaped coupling member attached to the output of the motor and a complementarily-shaped coupling member attached to the input shaft of the pump which frictionally engages the cone-shaped member.

18 Claims, 8 Drawing Figures

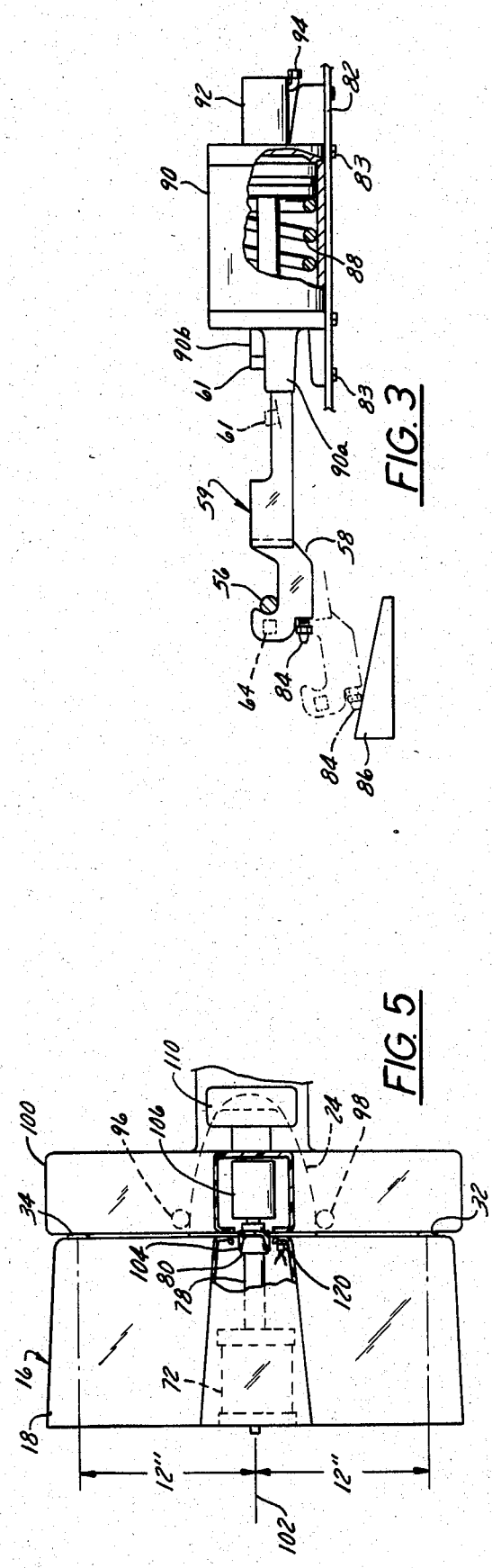
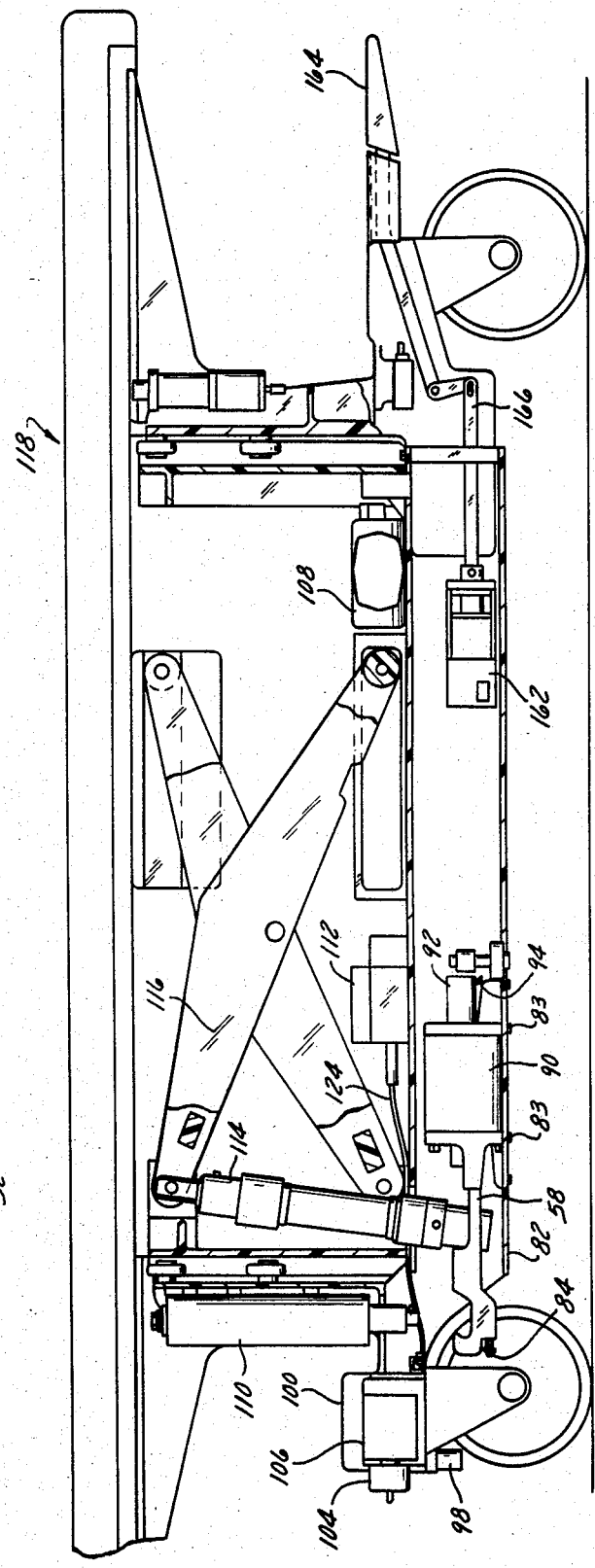
FIG. 3
FIG. 5
FIG. 4

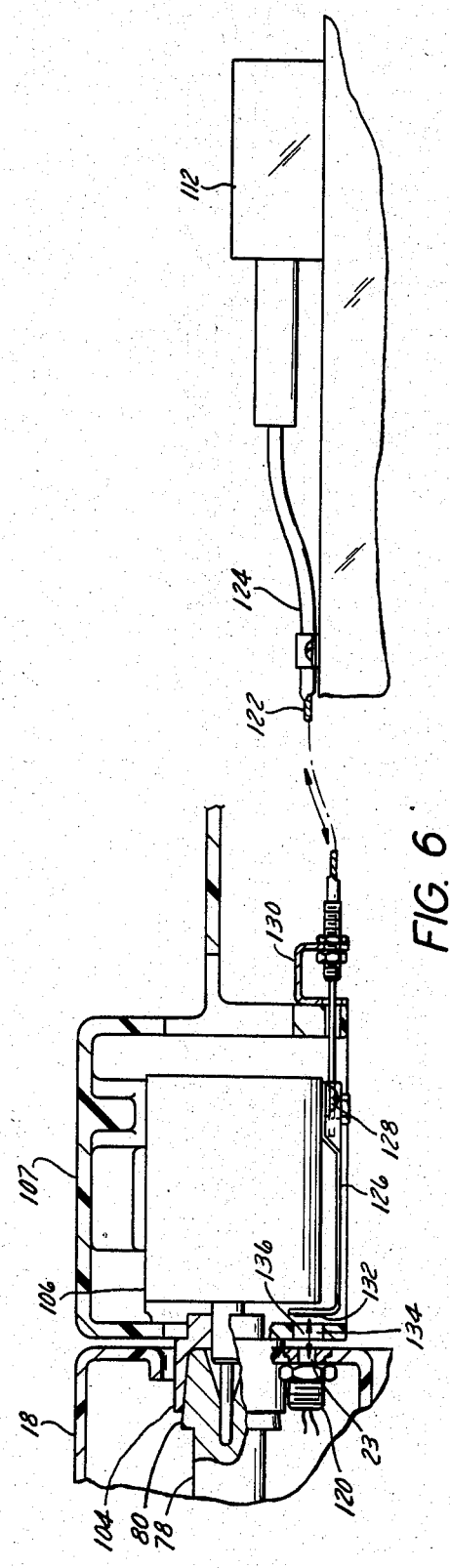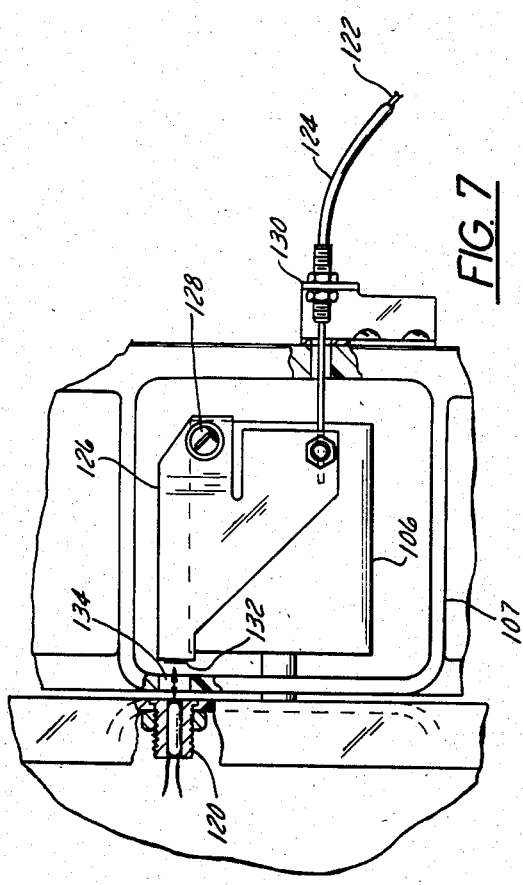
FIG. 6
FIG. 7

HYDRAULICALLY OPERATED, MOBILE PATIENT TRANSPORT TABLE USEFUL WITH A MAGNETIC RESONANCE SCANNER

BACKGROUND OF THE INVENTION

This invention relates to a magnetic resonance (MR) scanner apparatus. More specifically, this invention relates to a mobile, hydraulically-operated table useful with an MR scanner for transporting a patient from a preparation room to an MR examination room, and for retrievably positioning the patient within the bore of a scanner magnet.

The magnetic resonance phenomenon has been utilized in the past in high resolution MR spectroscopy instruments by structural chemists to analyze the structure of chemical compositions. More recently, MR has been developed as a medical diagnostic modality having application in imaging the anatomy, as well as in performing in vivo, non-invasive, spectroscopic analysis. As is now well known, the MR resonance phenomenon can be excited within a sample object, such as a human patient, positioned in a homogeneous polarizing magnetic field, by irradiating the object with radio frequency (RF) energy at the Larmor frequency. In medical diagnostic applications, this is typically accomplished by positioning the patient to be examined in the field of an RF coil having a cylindrical geometry, and energizing the RF coil with an RF power amplifier. Upon cessation of the RF excitation, the same or a different RF coil is used to detect the MR signals emanating from the patient volume lying within the field of the RF coil. The MR signal is usually observed in the presence of linear magnetic field gradients used to encode spatial information into the signal. In the course of a complete MR scan, a plurality of MR signals are typically observed. The signals are used to derive MR imaging or spectroscopic information about the object studied.

A whole-body MR scanner used as a medical diagnostic device includes a magnet, frequently of solenoidal design, to produce the polarizing magnetic field. The bore of the magnet is made sufficiently large to accommodate RF, gradient, and shim coil assemblies, as well as the torso of a patient to be examined. The scanner also includes a table which supports a cradle used to retrievably position the patient within the bore of the magnet. The table is aligned longitudinally with the bore of the magnet and disposed at the same height to facilitate the advancement of the cradle between a home position when the cradle is on the table and an advanced position when the cradle is in the magnet. A bridge structure in the bore supports the cradle and the patient when the cradle is in the advanced position.

It is desirable in an MR scanner apparatus to construct a table which is detachable from the magnet and which is mobile. The height of the table should be capable of adjustment to facilitate transfers of the patient from a gurney onto the cradle and to facilitate the movement of the cradle into and out of the magnet bore during an MR examination. A mobile table is desirable to, for example, promote efficient use of the scanner in that while one patient is undergoing examination, another could be readied in the preparation room. A mobile table is advantageous in situations where it is necessary to remove a patient from the magnet (as in an emergency) and to transport the patient with minimum delay to an area where assistance in the form of support equipment and care is available. It will be recognized that, due to the strong magnetic field (typically 1.5 tesla), support equipment must be located away from the magnet. This is necessary not only to ensure that the magnetic field does not adversely affect equipment operation, but to avoid magnetic objects in the vicinity of the magnet which could be drawn by the magnetic field toward the magnet. It will be further recognized that magnetic objects near the magnet may disturb the homogeneity of the field which could render the data collected unsuitable for use.

It is believed that, in the past, mobile tables have been used with computerized tomography (CT) apparatus. Such tables, however, are not suitable for use with MR scanner systems due in great part to the highly magnetic environment associated with MR. For example, the table must be constructed from non-magnetic materials. This requirement eliminates electric motors as energy sources to adjust table height. An alternative is to employ hydraulics as the power medium. Conventional hydraulic principles, however, cannot be easily implemented. One problem is the difficulty in transferring and storing energy in the mobile table because conventional hydraulic connectors have a tendency to leak when connected and disconnected repeatedly.

Another problem which must be addressed in a mobile MR table is that a docking device must be provided for aligning and holding the table in position while the patient is transferred into and out of the magnet in the course of an MR examination. Conventional proposals employed a long dock extension to ensure alignment of the cradle during transfer. This extension increased the size of the RF shield room used to provide bidirectional attenuation of RF energy and was bulky and inconvenient to use. Another factor which must be considered is the requirement to undock the table in the event of an emergency.

In a mobile table there is also the need to monitor table operational parameters such as positive docking of the table to the magnet, and hydraulic pressure. These functions must be accomplished without electrical connections between the table and the magnet.

It is an object of the invention to provide means for transferring hydraulic energy to a mobile table, which is part of an MR scanner, without utilizing conventional hydraulic connections.

It is a further object of the invention to provide means for monitoring operational parameters in a table of an MR scanner without employing electrical connections between the table and magnet.

It is still another object of the invention to provide a docking mechanism for securing a table to a magnet of an MR scanner.

SUMMARY OF THE INVENTION

In accordance with the invention there is provided an MR scanner apparatus including a magnet for producing a polarizing magnetic field and a mobile, hydraulically operated patient transport table. The scanner further includes a hydraulic motor disposed at the base of the magnet and a hydraulic pump disposed at the base of the table. The hydraulic motor and pump are operatively coupled to enable transfer of energy from the motor to the pump without use of hydraulic connections therebetween, when the motor is energized. In the preferred embodiment, the coupling is implemented with a cone-shaped coupling member attached to the output of the motor and a complementarily-shaped coupling member attached to the input shaft of the pump which frictionally engages the cone-shaped member.

BRIEF DESCRIPTION OF THE DRAWINGS

The features of the invention believed to be novel are set forth with particularly in the appended claims. The invention itself, however, both as to its organization and method of operation, together with further objects and advantages thereof, may best be understood by reference to the following description taken in conjunction with the accompanying drawings in which:

FIG. 3 is a side view of a latch cylinder assembly, in accordance with the invention;

FIG. 4 is a side view of a patient support table which forms part of an MR scanner apparatus, with the covers removed;

FIG. 5 is a top view, in the docked state, of the forward portion of the table depicted in FIG. 4, and the power transfer and docking assembly depicted in FIG. 2;

FIG. 6 is a partial side view of the table showing a cut-away view of the hydraulic pump housing and the means for monitoring accumulator pressure;

FIG. 7 is a bottom view of the hydraulic pump depicting in greater detail the means for monitoring accumulator pressure.

DETAILED DESCRIPTION OF THE INVENTION

Figure 1:
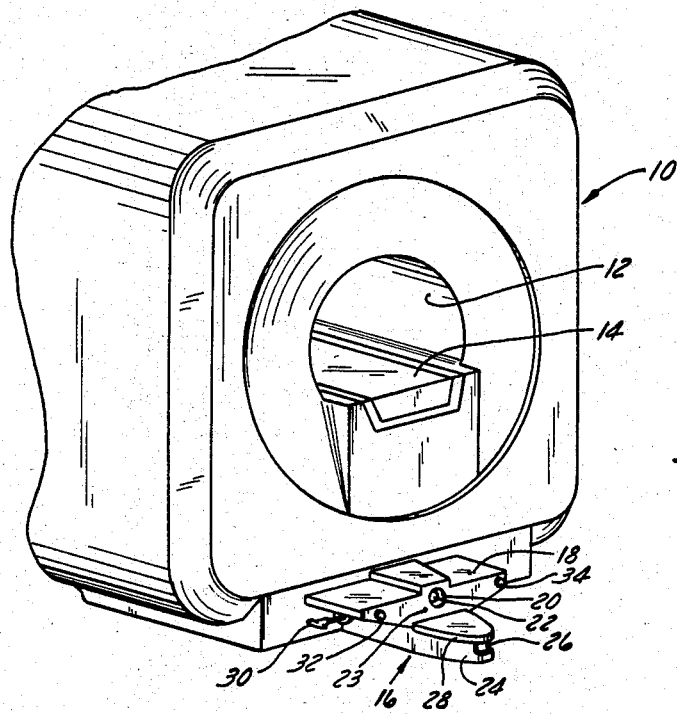
FIG. 1 depicts partially a magnet housing and an inventive power transfer and docking assembly.

FIG. 1 depicts a housing 10 within which is disposed a magnet, typically of superconductive, solenoidal design, for producing a homogeneous polarizing magnetic field within a bore 12 of the magnet. A bridge structure 14, disposed within the bore, supports a patient cradle (not shown) on which the patient rests during an MR examination. A power transfer/docking assembly, generally designated 16, is disposed at the base of housing 10, centered generally below magnet bore 12. The docking assembly comprises an upper cover 18 having a circular opening 20 through which a hydraulic pump mounted to an MR mobile table engages a hydraulic motor coupling 80 housed in the docking assembly, as will be more fully discussed hereinbelow. Upper cover 18 includes an opening 23 through which a light-emitting diode/photo-transistor assembly monitors the pressure in a hydraulic accumulator disposed on the table. A lower cone-shaped portion 24 of docking assembly 16 houses a docking mechanism and includes an opening 26, below a cover 28, through which a hook, which is part of a latch cylinder assembly (described subsequently), engages the docking mechanism, when the table is docked to the magnet. A handle 30 is used to manually undock the table in the event of a hydraulic system malfunction. A pair of docking points 32 and 34, against which the table rests when docked, formed of a firm resilient material (such as urethane), is provided on upper cover 18 to either side of opening 20.

Figure 2:
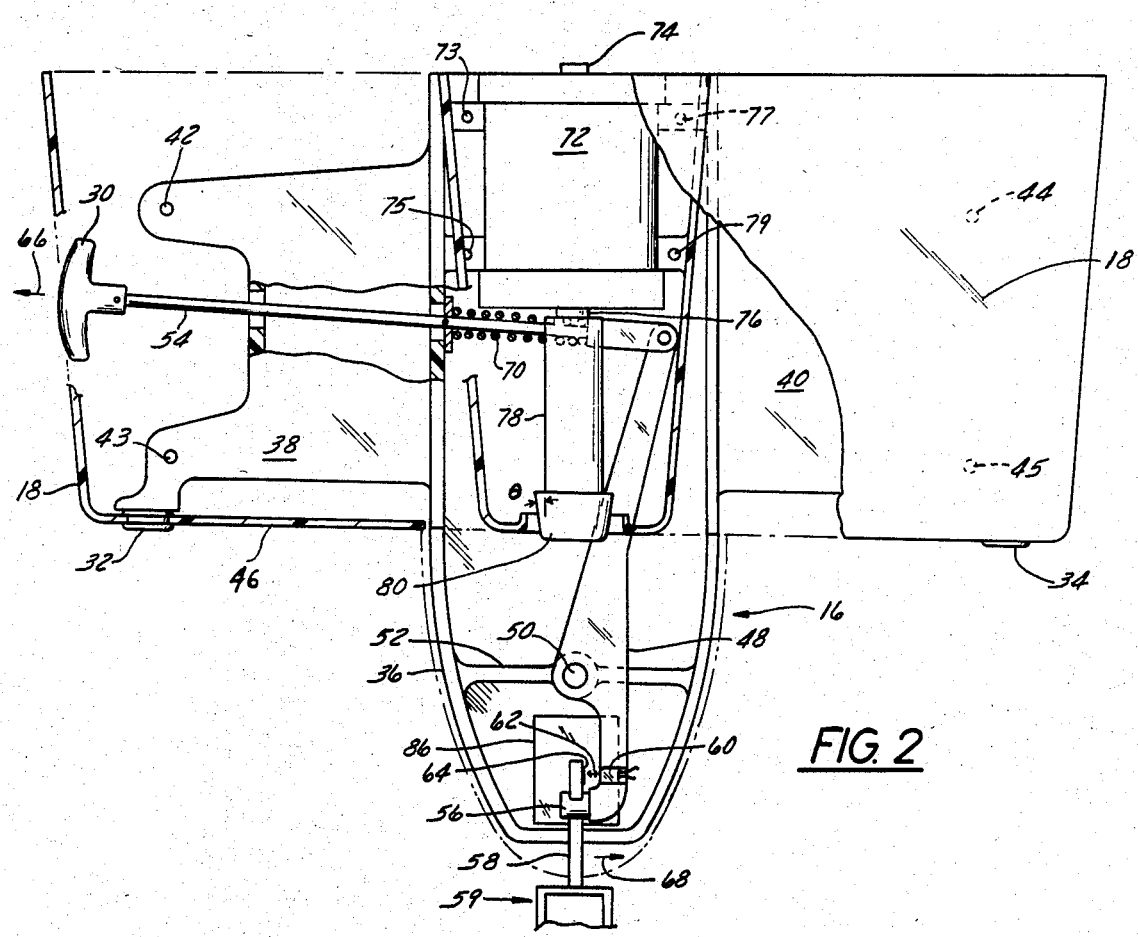
FIG. 2 is a top view of the inventive power transfer and docking assembly with the covers removed.

Reference is now made to FIG. 2 which depicts a top view of docking and power transfer assembly 16 shown with covers 18 and 28 (FIG. 1) removed. In FIGS. 1 and 2, as in subsequent figures, like parts are assigned like reference numbers. Continuing now with reference to FIG. 2, there is shown a cone-shaped cast aluminum frame 36 positioned such that the cone or forward end faces away from the magnet housing, while the base of the cone is positioned against the magnet housing. To either side of frame 36 and forming an integral part thereof are extensions 38 and 40, the forward portions of which comprise docking points 32 and 34, respectively. Extensions 38 and 40 include openings 42-45 by means of which cover 18 is bolted to frame 36. Although not shown in FIG. 1, docking assembly 16 is disposed in a plastic housing 46 shown partially cut away in FIG. 2.

A lever 48, FIG. 2, which forms part of the latching mechanism is pivoted at a point 50 to a transverse frame member 52 which is located at the forward end of frame 36. One end of lever 48 includes a pin member 56 shown engaged to a latch hook 58 which is part of a latch cylinder assembly 59 (to be discussed) mounted to the table, as would be the case when the table is docked. Positive docking of the table is detected by a light-emitting diode (LED)/photo-transistor assembly 60 comprised of two LED's and two photo transistors. The light emitted by the LED's is reflected, as suggested by bidirectional arrow 62, by a reflective area 64 (best seen in FIG. 3) fabricated on the side of the latch-hook and is detected by the photo-transistors. The photo-transistor outputs are used to provide an indication of positive docking on an operator console display panel (not shown). Dual LED's and photo-transistors are used for redundancy so that positive docking indication is not obtained unless both photo-transistor devices detect the reflected light.

Continuing with reference to FIG. 2, manual undocking is achieved by pulling handle 30, attached to a rod 54, in the direction indicated by arrow 66. Rod 54 is pivotably connected at its other end to lever 48 such that movement of the rod in the direction of the arrow causes lever 48 to pivot about point 50 in the direction of arrow 68 such that latch hook 58 disengages from pin 56. Rod 54 is returned to its detent position by a spring 70 through which the rod is threaded.

Continuing with further reference to FIG. 2, a hydraulic motor 72 having an input hydraulic fitting 74 and an output shaft 76 is mounted near the base of frame 36 by means of bolts 73, 75, 77, and 79. The hydraulic motor is powered from a remote electrically driven hydraulic pump (not shown). The pump and the electric motor are located away from the magnet in an adjacent control room. The pump is coupled to motor 72 by a length of hydraulic hose (not shown). The output of the hydraulic motor is taken from a flexible, coupling element 78 having a conically-shaped engaging surface 80. The coupling member is bidirectionally flexible such that its transverse flexibility aids in docking, while its axial elasticity ensures good frictional contact to effectively transfer power to a hydraulic pump mounted on the table.

The manner in which the hydraulic motor transfers power to the hydraulic pump in the table and the manner in which docking of the table is achieved will be described next. The docking of the table will be described first so that initial reference is made to FIGS. 2, 3, and 4. FIG. 3 depicts a partially cut-away view of spring-loaded, hydraulically operated latching mechanism assembly 59, which is mounted to a plate 82 in the table, as shown in FIG. 4, by means of bolts 83. The latch assembly is provided at its forward end below hook 58 with a rounded head bolt 84. When the table is to be docked to the magnet, bolt 84 slides (as suggested by the partial dash-line depiction of the latch cylinder assembly) up a wedge 86 mounted in the cone-shaped end of the docking assembly. The upward movement of hook 58 continues until a detent member 61 (which is part of the latch hook) is elevated past an extension 90a of enclosure 90 allowing a spring 88 to retract latch hook 58 so that it engages pin 56. The rate at which the latch hook is retracted is controlled by meter flow of the hydraulic fluid flow from the cylinder 92 through fitting 94. In the docked state, detent member 61 rests against a portion 90b of the enclosure. Spring 88, housed in enclosure 90 (shown partially cut away in FIG. 3), exerts a force of, for example, 200 lbs. to hold the table in place. The undocking is accomplished by compressing the spring with a hydraulic cylinder 92 energized through a fitting 94 until detent member 61 slides off extension 90b, returning the latch hook to its detent position, indicated by dashed lines in FIG. 3.

The table is guided into docking position with the aid of two vertical pins 96 and 98 mounted below a transverse plate 100 at the forward end of the table. A top view of the pins is shown in FIG. 5, which depicts a top view of the forward portion of the table shown in FIG. 4 and the docking and power transfer assembly shown in FIGS. 1 and 2. During the docking approach, the pins slide along cone-shaped guide 24 of the docking assembly until docking points 32 and 34 are in contact with plate 100, at which time the latching mechanism becomes operative. The cone-shaped guide and pins allow the table to be easily docked even in the presence of misalignment of the table relative to the docking assembly during the docking approach.

Continuing now with reference to FIG. 5, docking points 32 and 34 are spread as far as practical to keep the clamping force to a minimum. In one embodiment it was found that a separation of 12 inches from center line 102 was found satisfactory. With a separation of 12 inches and a force of 200 pounds exerted by spring 88, a force of 48 pounds is required at a distance of 50 inches away from the latch point to move the table off seat. This has been found adequate to avoid forcing the table out of position as a result of accidental bumping. Of course, if desired, either the separation of the clamping points or the spring force can be changed to modify the safety margin.

The manner in which power is transferred from the hydraulic motor to the table hydraulic system and stored therein will now be described with reference to FIGS. 4 and 5. When the table is docked to the magnet, in the manner described hereinbefore, cone-shaped engaging portion 80 of flexible coupling member 78 engages a complementary shaped engaging member 104 mounted to the shaft of a hydraulic pump 106 located on transverse plate 100 at the forward end of the table. The cone-shaped coupling performs a dual function in that it acts as a self-centering pilot to aid in the automatic docking, as well as a power transfer point. The exterior surface of motor coupling 80 frictionally engages the interior surface of pump coupling 104 member. The optimum engaging angle $\theta$, as indicated in FIG. 2, has been found to be approximately 7°, although variations from this value can also result in operative embodiments. Power is transferred to pump 106 by rotation of motor coupling member 78. The pump operates to charge a hydraulic accumulator 108 from a hydraulic fluid reservoir 110. The hydraulic energy stored in the accumulator is used to operate cylinder 92 used to undock the table from the magnet. Energy is supplied to fitting 94 of cylinder 92 from the accumulator through an accumulator monitoring valve 112.

Hydraulic energy supplied by motor 72 is used to activate a table lift hydraulic cylinder 114 coupled at one end to a structural member of the table and its other end to a scissor jack assembly, generally designated by reference numeral 116 in FIG. 5, which supports a table top 118. Extension of the cylinder piston has the effect of raising the table, while retraction of the piston lowers the table.

Although the accumulator is automatically charged upon docking of the table with the magnet, it is, nonetheless, desirable to monitor the state of the accumulator to ensure that sufficient energy is stored to operate the undocking mechanism. The manner in which this is accomplished will now be described with reference to FIGS. 6 and 7, which depict, respectively, a side view of hydraulic pump 106, and a bottom view of the pump. The state of the accumulator is monitored electronically by two LED/photo-transistor assemblies generally designated 120, mounted at the base of the magnet in the docking and power transfer assembly. A drop in accumulator pressure is sensed by accumulator monitor valve 112 which activates an internally-disposed plunger connected to one end of a cable 122 housed within a sleeve 124. The other end of cable 122 is fastened to a belcrank 126 mounted pivotally at point 128 to the bottom of pump 106. Sleeve 124 is secured at its ends to a bracket 130 on the pump housing and to the case of valve 112. In this manner, cable 122 is free to move bidirectionally within sleeve 124 when the plunger is actuated to indicate normal or low accumulator pressure states. In the low pressure state, the cable operates to position a reflectively coated flag 132 on the belcrank in optical communication with LED/photo-transistor assembly 120, through an opening 134 in pump housing 107, as suggested by bidirectional arrow 136. Upon detection of the flag, the hydraulic motor is activated so that accumulator pressure is restored to its normal level. When the pressure reaches the correct level, valve 112 retracts cable 122 causing the belcrank to rotate thereby interrupting the optical link. This has the effect of inactivating the hydraulic motor.

Figure 8:
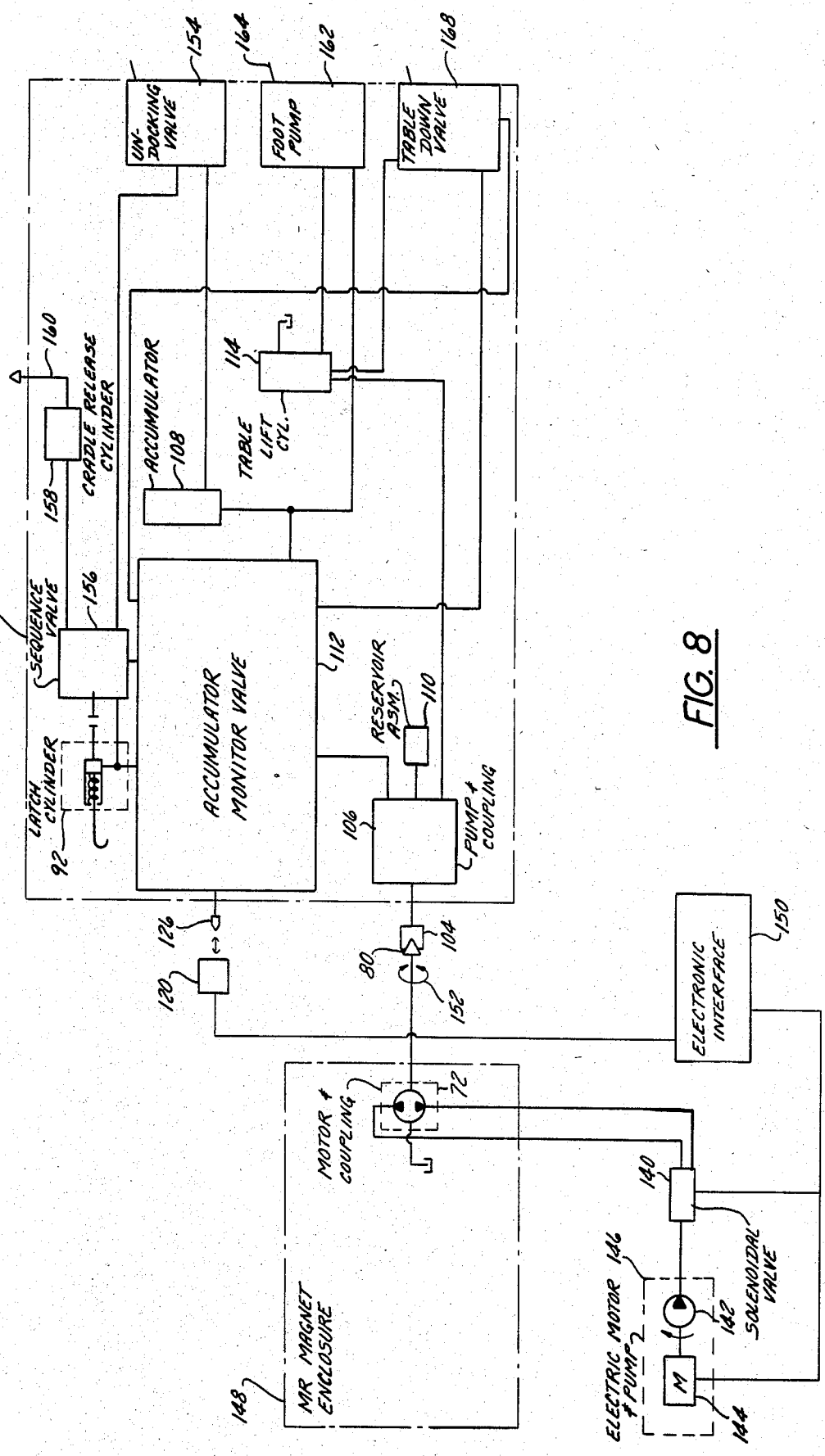
FIG. 8 is a hydraulic block circuit schematic of the hydraulic system in an MR scanner.

FIG. 8 depicts a hydraulic block circuit schematic of a hydraulic system in an MR scanner with respect to which general system operation and element interconnection will be described. Many of the elements have been described hereinbefore so that the same reference numbers will be used to identify previously discussed elements. Thus, hydraulic motor 72 is energized through a solenoidal valve 140 by a hydraulic pump 142 which is driven by an electric motor 144. The electric motor and the hydraulic pump, collectively designated 146, are located physically away from the MR magnet enclosure 148 which houses hydraulic motor 72. Solenoidal valve 140 operates under control of an electronic interface 150 to select the direction in which motor 72 rotates. As suggested by bidirectional arrow 152, motor 72 is capable of clockwise and counterclockwise rotation. Pump 106, having its coupling member 104 engaged to motor coupling member 80, rotates in the same direction as the motor. In operation, rotation in the clockwise direction, for example, results in pump 106 energizing table lift cylinder 114 to raise the table. Rotation in the counterclockwise direction results in accumulator 108 being charged from reservoir 110, provided LED/photo-transistor assembly 120 detects flag 126 enabling electronic interface 150 to activate electric motor 144. As discussed hereinbefore, flag 126 is operated by accumulator monitor valve 112 which senses accumulator pressure. It will be, of course, recognized that the hydraulic functions described could be implemented to operate with the motor directions opposite to those discussed.

The energy stored in accumulator 108 is used to operate latch cylinder 92 to undock the table when undocking valve 154 is operated. The accumulator volume is sized to provide sufficient energy to complete two undocking operations. A sequence valve 156 is mechanically linked to latch cylinder 92 and controls the operation of a cradle release cylinder 158 which is also operated by energy stored in the accumulator. The function of cradle release cylinder is to retract a pin, suggested by arrow 160, which releases a patient cradle (not shown) to move off the table into the bore of the magnet when the table is docked.

A foot pump 162, mechanically coupled to a foot pedal 164 by a linkage 166 (FIG. 4), is used to energize table lift cylinder 114 to raise the table when the latter is not docked to the magnet. The foot pump can also be used to charge accumulator 110. This is accomplished by continuing operation of the foot pump after the table has reached its maximum height. A table-down valve 168 is used to release fluid from table lift cylinder 114 in a controlled manner to manually lower the table with gravity assistance.

From the foregoing, it will be appreciated that there is provided in accordance with the invention a means for transferring hydraulic energy to a mobile table which is part of an MR scanner without utilizing conventional hydraulic connections between the power source and the energy storage unit. Means are also provided for monitoring table operational parameters through optical coupling devices without employing direct electrical connections between to the magnet structure to which it is docked by an inventive self-guiding power transfer and docking assembly.

While this invention has been described with reference to particular embodiments and examples, other modifications and variations will occur to those skilled in the art in view of the above teachings. Accordingly, it should be understood that within the scope of the appended claims the invention may be practiced otherwise than is specifically described.

The invention claimed is:

1. An MR scanner system including a magnet for producing a polarizing magnetic field and having a bore for receiving a patient, a mobile, hydraulically-operated patient transport table, said MR scanner system further comprising:
   a hydraulic motor disposed at the magnet;
   a hydraulic pump disposed at the table; and
   means for operatively coupling said hydraulic motor to said hydraulic pump so as to transfer energy from the motor to the pump without requiring a hydraulic connection therebetween, when said motor is energized.

2. The MR scanner of claim 1 wherein said means for coupling comprises:
   a first coupling member attached to the output shaft of said motor; and
   a second coupling member attached to the input shaft of said pump, said second coupling member being complementarily shaped to receive and frictionally engage said first coupling member.

3. The MR scanner of claim 2 wherein said first coupling member attached to the output shaft of said motor comprises a cone-shaped coupling member, wherein the engaging angle of the cone-shaped coupling member is approximately 7 degrees.

4. The MR scanner of claim 2 wherein said cone-shaped coupling member is comprised of a flexible material.

5. The MR scanner of claim 2 further comprising accumulator means coupled to said pump for storing energy transferred to the pump by said motor.

6. The MR scanner of claim 1 further comprising an accumulator means coupled to said pump for storing energy transferred to the pump by said motor.

7. The MR scanner of claim 6 further comprising means coupled to said accumulator means for sensing the pressure therein, for activating said hydraulic motor when the pressure decreases below a predetermined level, and for disabling said motor when the pressure is restored to the correct level.

8. The MR scanner of claim 7 wherein said means for sensing comprises:
   flag means having a first state indicative of a pressure in said accumulator below a predetermined level and a second state indicative of normal accumulator pressure;
   an accumulator monitor valve coupled at its input to said accumulator and at its output to said flag means so as to alter the state thereof between said first and second states; and
   means responsive to the first stage of said flag means for activating said motor, and responsive to the second state of said flag means for disabling said motor.

9. The MR scanner of claim 1 including means for releasably docking the patient transport table to the magnet, said means for docking comprising:
   a latch cylinder assembly mounted to the table, said assembly including hook means; and
   a docking assembly mounted at the base of the magnet including pin means for engaging said hook means, said latch cylinder assembly including spring means coupled to said hook for maintaining said pin and hook means engaged thereby to dock the table to the magnet.

10. The MR scanner of claim 9 wherein said latch cylinder assembly further comprises hydraulically actuated cylinder means for compressing said spring means thereby to disengage said hook means for said pin means to undock the table.

11. The MR scanner of claim 9 further comprising means for detecting positive docking of the table, said means for detecting comprising flag means on said hook means and means for detecting said flag means when said pin and hook means are engaged.

12. The MR scanner of claim 11 wherein said flag and detecting means comprise, respectively, a reflective region and a light-emitting diode/photodiode assembly.

13. An MR scanner system including a housing supporting a magnet for producing a polarizing magnetic field and having a bore for receiving a patient, a mobile, hydraulically-operated patient transport table, said MR scanner system further comprising:
   a power transfer and docking assembly secured to said housing;

docking means fastened to said mobile table for engaging said power transfer and docking assembly so as to releasably dock said table to said housing;

hydraulic motor means disposed in said power transfer and docking assembly;

hydraulic pump means disposed on said table; and means for operatively coupling said hydraulic motor means to said pump means, when said table is docked so as to transfer energy from said hydraulic motor means to said hydraulic pump means without requiring a hydraulic connection therebetween, when said hydraulic motor means is energized.

14. The MR scanner of claim 13 wherein said means for coupling comprises:

a first coupling member attached to the output shaft of said motor; and a second coupling member attached to the input shaft of said pump, said second coupling member being complementarily shaped to receive and frictionally engage said first coupling member.

15. The MR scanner of claim 14 wherein said first coupling member attached to the output shaft of said motor comprises a cone-shaped coupling member, wherein the engaging angle of the cone-shaped coupling member is approximately 7 degrees.

16. The MR scanner of claim 14 wherein said cone-shaped coupling member is comprised of a flexible material.

17. The MR scanner of claim 14 further comprising accumulator means coupled to said pump for storing energy transferred to the pump by said motor.

18. The MR scanner of claim 13 further comprising an accumulator means coupled to said pump for storing energy transferred to the pump by said motor.

* * * * *